2-Amino-2,3-dimethylbutyronitrile (273.27 g, 94% purity, 2.287 mol) is added to a stirred solution of 2,3-pyridinedicarboxylic anhydride 333.3 g, 0.98 mol) in 4-picoline (1600 mL) under a nitrogen atmosphere while maintaining the temperature of the reaction mixture at 8° to 12° C. The resulting mixture is stirred for one and one-half hours at 8° to 12° C. Analysis of the reaction mixture by high performance liquid chromatography shows the formation of the desired 2-[(1-carbamoyl-1,2-dimethylpropyl)carbamoyl]nicotinic acid in 84.1% yield. The product is isolated by dilution of the reaction mixture with toluene (1600 mL), and extraction into aqueous sodium hydroxide (800 mL, 50% NaOH, in 532 mL water) at 35° to 40° C. The basic extract is washed with toluene (1600 mL) at 35° to 40° C., and the basic solution of the product (1778.0 g) is separated off. Additional aqueous sodium hydroxide (80 g, 50%) is added to one-half of the stirred basic extract and the solution heated to 40° C. Aqueous hydrogen peroxide (221 g, 50% 6.5 mol) is then added over one hour and 15 minutes at 40° to 45° C. and the reaction mixture is allowed to stir at 40°–45° C. for two hours. The reaction mixture is then heated to 70° C. and allowed to stir for two hours to complete the formation of the 2-(4-isopropyl-4-methyl-5-oxo-2-imidazolin-2-yl)nicotinic acid which is isolated by acidification, and filtration.

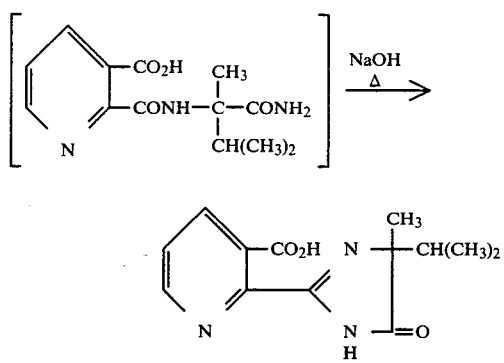

EXAMPLE 8

Postemergence herbicidal evaluation of test compounds

The postemergence herbicidal activity of the compounds prepared by the process of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantities to provide the equivalent of about 0.16 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table IV below.

| Rating System | % Difference in Growth from the Check* |
|---|---|
| 0 - No Effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green foxtail | (Setaria viridis) |
| Purple Nutsedge | (Cyperus rotundus L.) |
| Wild Oats | (Avena fatua) |
| Quackgrass | (Agropyron repens) |
| Field Bindweed | (Convolvulus arvensis L.) |
| Cocklebur | (Xanthium pensylvanicum) |
| Morningglory | (Ipomoea purpurea) |
| Ragweed | (Ambrosia artemisiifolia) |
| Velvetleaf | (Abutilon theophrasti) |
| Barley | (Hordeum vulgare) |
| Corn | (Zea mays) |
| Rice | (Oryza sativa) |
| Soybean | (Glycine max) |
| Sunflower | (Helianthus annus) |
| Wheat | (Triticum aestivum) |

TABLE IV

| POST-EMERGENCE TESTS - RATES IN KG/HA | | | | | | | | |
|---|---|---|---|---|---|---|---|---|
| Compound | RATE | BARNY ARDGR | GREEN FOX | P NUT SEDGE | WILD OATS | QUACK GRASS | FLD D IHOWO | MRNGL RY SP |
| 2-(4-Isopropyl-4- | 10.000 | 9.0 | 9.0 | 9.0 | 9.0 | | | 7.0 |
| methyl-5-oxo-2- | 2.000 | 9.0 | 9.0 | 9.0 | 9.0 | | | 0.0 |
| imidazolin-2-yl)- | 1.000 | 9.0 | 9.0 | 9.0 | 9.0 | 9.0 | 0.0 | 0.0 |
| nicotinic acid | .500 | 9.0 | 9.0 | 8.7 | 9.0 | 9.0 | 9.0 | 0.0 |
| | .250 | 8.9 | 9.0 | 8.8 | 9.0 | 9.0 | 9.0 | 0.9 |
| 2-(4-Isopropyl- | 0.000 | 9.0 | 9.0 | 9.0 | 9.0 | 9.0 | 9.0 | 9.0 |
| 4-methyl-5-oxo- | 4.000 | 9.0 | 9.0 | 9.0 | 9.0 | 9.0 | 9.0 | 0.5 |
| 2-imidazolin-2- | 2.000 | 9.0 | 9.0 | 0.5 | 9.0 | 9.0 | 9.0 | 0.3 |
| yl)-3-quinoline- | 1.000 | 9.0 | 9.0 | 0.3 | 9.0 | 8.9 | 8.7 | 0.3 |
| carboxylic acid | .800 | 9.0 | 8.8 | 6.8 | | 8.8 | 8.8 | 6.8 |
| | .500 | 8.9 | 8.9 | 7.6 | 9.0 | 8.6 | 8.3 | 7.7 |

| Compound | RAGWE ED | VELVE TLEAF | S BAR LY LA | CORN FIELD | RICE, NATO | SOYBE AN HI | SUNFL R XXX | S WHE AT ER |
|---|---|---|---|---|---|---|---|---|
| 2-(4-Isopropyl-4- | 9.0 | 9.0 | | | | | | |

6-[3-AMINO-1-(4-TOLYL)PROP-1E-ENYL]PYRIDINE-2-CARBOXYLIC ACID DERIVATIVES HAVING ANTIHISTAMINIC ACTIVITY

The present invention relates to new chemical compounds exhibiting antihistamine activity, to processes for preparing them, to novel intermediates involved in their preparation, to pharmaceutical compositions containing them and to their use in medicine.

U.S. Pat. No. 2,717,023 discloses a group of pyridyl propenylamines with antihistamine activity, the most outstanding of which is the compound named (E)-1-(4-methylphenyl)-1-(2-pyridyl)-3-pyrrolidinoprop-1-ene and hereinafter referred to by its generic name, triprolidine. Triprolidine has gained widespread clinical acceptance and is one of the most potent antihistamines available.

The antihistamines now in use, eg. diphenhydramine, the pheniramines, pyrilamine, promethazine and triprolidine may cause sedation or drowsiness in some patients.

A novel group of compounds having antihistamine activity has now been discovered. These compounds have been found to be substantially free from sedative effects and have little or no anticholinergic effects.

Accordingly this invention provides the compounds of formula I.

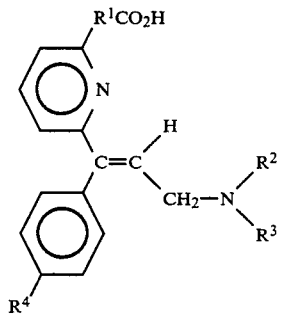

or corresponding straight and branched lower alkyl (1–4 carbon atoms) esters and salts thereof; wherein $R^1$ is $(CH_2)_n$, n is an integer 0 to 7, or $(CH_2)_a CH=CH-(CH_2)_b$, a and b are independently 0 to 5 and the sum of a and b does not exceed 5; $R^2$ and $R^3$ are the same or different and can be hydrogen, $C_{1-4}$ alkyl or taken together with the nitrogen together with the nitrogen to which they are attached form a nitrogen containing heterocyclic ring having four to six ring members; $R^4$ is hydrogen, halogen, $C_{1-4}$ alkoxy or $C_{1-4}$ alkyl optionally substituted by one to three halogen atoms; provided that when $R^1$ is $-CH=CH-$ and $NR^2R^3$ is pyrrolidine, $R^4$ is not $-CH_3$ or $-CF_3$.

If the carboxylic acid side chain is placed in any position on the pyridine ring other than that shown in FIG. 1 (i.e., the 2 position) or the configuration about the central double bond (from the carbon bonded to the pyridine and phenyl rings) is Z rather than E as shown above, the antihistaminic activity of such a compound is significantly reduced. That is, its antihistaminic activity is below the point of practical value.

Esters of the compounds of the formula (I) are also useful intermediates in the preparation of the parent compounds of the formula (I). Salts of the compounds of the formula (I) may be either acid addition salts or salts formed with the carboxylic acid group. Pharmaceutically acceptable salts are preferred.

Preferred compounds of the formula (I) include:

| Compound | |
|---|---|
| A | 3-{6-[3-Pyrrolidino-1-(4-tolyl)prop-1E—enyl]-2-pyridyl}propionic acid |
| B | (E)—3-{6-[3-Dimethylamino-1-(4-tolyl)prop-1E—enyl]-2-pyridyl}acrylic acid |
| C | (E)—3-{6-[3-pyrrolidino-1-(4-methoxyphenyl)prop-1E—enyl]-2-pyridyl}acrylic acid |
| D | (E)—3-{6-[1-(4-chlorophenyl)-3-pyrrolidinoprop-1E—enyl]-2-pyridyl}acrylic acid |
| E | (E)—3-[6-(1-phenyl-3-pyrrolidinoprop-1E—enyl)-2-pyridyl]acrylic acid |
| F | 6-[3-pyrrolidino-1-(4-tolyl)prop-1E—enyl]pyridine-2-carboxylic acid |

1. A method for preparing compounds of formula (I) comprises reacting a compound of (II) with a compound of formula (III) by the Wittig method (see *Organic Reactions*, 14, 270–490 (1965) and *Pure and Applied Chemistry*, 9, 245–254 (1964)).

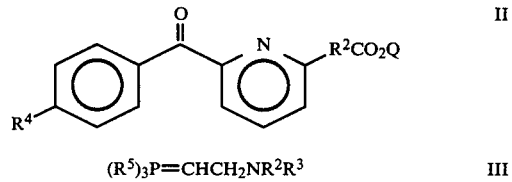

$$(R^5)_3P=CHCH_2NR^2R^3 \quad \text{III}$$

wherein $R^1$, $R^2$, $R^3$ and $R^4$ are the same as defined for formula (I), $R^5$ is aryl such as phenyl or lower alkyl (1 to 4 carbons) and Q is a lower alkyl group (1–4 carbons) or an alkali metal such as lithium or sodium. The reaction may be followed by deprotection of the carboxyl group as necessary. The product may be converted to an acid addition salt, a salt of the carboxylic acid, or an ester by conventional methods.

The compound of formula (III) is a Wittig reagent which may be prepared by treatment of a phosphonium salt (IV) with a strong base, for example an alkyl or aryl lithium compound or sodium hydride in a suitable solvent, for example toluene or tetrahydrofuran.

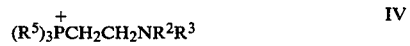

wherein $R^2$ and $R^3$ are as defined above and $R^5$ is lower alkyl on phenyl. The phosphonium salts (IV) are prepared by known methods (e.g., see British Patent No. 1,161,201).

Compounds of formula (II) in which $R^1$ is $-CH=CH-$ (trans) may be prepared by reacting a compound of formula (V) wherein $R^4$ is as defined above with an acrylate ester (VI) wherein $R^6$ is a lower alkyl group (1–4 carbon atoms) in presence of a catalyst consisting of palladium acetate and a triarylphosphine and a tertiary amine such as triethylamine or tributylamine. Optionally a solvent such as acetonitrile may be used and the reactants may with advantage be heated together in a sealed pressure vessel (e.g., see R. F. Heck et al., *J. Org. Chem.*, 43, 2947 (1978)).

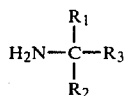

(III)

wherein $R_1$, $R_2$ and $R_3$ are as described above at from 5° to 45° C., the improvement comprising carrying out the reaction in a solvent system containing a minimum of 4 molar equivalents of pyridine, 4-picoline, 2-picoline, 3-picoline, mixed picolines, quinoline, or a lutidine, used either as the reaction solvent or as a co-solvent, with other organic solvents, for several hours.

3. A method according to claim 2, wherein the reaction solvent is 6 to 10 molar equivalents of pyridine, 4-picoline, 2-picoline, mixed picolines or quinoline.

4. A method according to claim 2, wherein the reaction solvent is a mixture of toluene containing 6 to 10 molar equivalents of pyridine, 4-picoline, 2-picoline, mixed picolines or quinoline.

5. A method according to claim 2, wherein the reaction is conducted in a temperature range of 5° to 30° C.

6. A method according to claim 5, for the preparation of 2-[(1-carbamoyl-1-2-dimethylpropyl)-carbamoyl]-nicotinic acid.

7. A method according to claim 5, for the preparation of 2-[(1-carbamoyl-1,2-dimethylpropyl)-carbamoyl]3-quinolinecarboxylic acid.

8. A method according to claim 5, for the preparation of 2-[(1-cyano-1,2-dimethylpropyl)carbamoyl]-nicotinic acid.

9. A method according to claim 5, for the preparation of 2-[(1-cyano-1,2-dimethylpropyl)carbamoyl]3-quinolinecarboxylic acid.

* * * * * about 0.025 to 1.0 mg per kilogram body weight per day; preferably from 0.04 to 0.24 mg/kg. For example a typical dose for a human recipient of compound A is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from about 0.014 to 0.08 mg/kg body weight; for example, a typical sub-dose (which can be given in a pharmaceutical formulation such as a tablet, capsule or syrup) for a human recipient is about 2 mg.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestant pseudoephedrine or phenylpropanolamine, an antitussive such as codeine, an analgesic such as acetaminophen, an antiinflammatory and an antipyretic such as aspirin, or an expectorant such as guaifenesin. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrat, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, phosphoric, maleic, salicylic, p-toluenesulfonic, tartaric, citric, methanesulfonic, formic, malonic, succinic, naphthalene-2-sulfonic and benzenesulfonic. Also pharmaceutically acceptable salts can be prepared as alkaline metal or alkaline earth salts, such as sodium, potassium or calcium salts of the carboxylic acid group.

The following Examples are provided by the way of illustration of the present invention and should in no way be construed as a limitation thereof. All temperature indicated are in degrees Celsius.

EXAMPLE 1:
3-{6-[3-Pyrrolidino-1-(4-tolyl)prop-1E-enyl]-2-pyridyl} propionic acid Butyllithium (50 mL, 1.65M in hexane) was added under nitrogen to a stirrer suspension of 2,6-dibromopyridine (19.5 g) in dry ether (200 mL) at −50°. After 0.75 hr a solution of 4-tolunitrile (10 g) in ether (50 mL) was added; stirring was continued at −50° for 3 hrs. The mixture was allowed to warm to −30° and treated with hydrochloric acid (200 mL, 2M). The precipitated solid was collected, washed with water, and recrystallized from aqueous ethanol. The 2-bromo-6-(4-toluoyl)pyridine formed colourless needles (12.2 g) m.p. 97°–98°.

A mixture of 2-bromo-6-(4-toluoyl)pyridine (200 g), ethylene glycol (85 mL), p-toluenesulphonic acid (32 g) and benzene (11 mL) was boiled under a Dean/Stark trap until water collection had become very slow (about 20 mL collected in 16 hours).

The cooled solution was poured into ice/water containing sodium carbonate (100 g) with stirring. The benzene layer was separated, washed with water, dried with sodium sulphate and evaporated to about 500 mL. Cooling gave a first crop of 2-(6-bromo-2-pyridyl)-2-(4-tolyl)-1,3-dioxolan (compound 1), m.p. 113°–114° (170 g). Dilution with petroleum ether gave a second crop, m.p. 109°–112° (34 g). The residue after evaporation (31 g) was recycled.

A solution of compound 1, vide supra, (70 g) in dry toluene (800 mL) was added dropwise during 5 hr to a stirred solution of butyllithium (1.6M in hexane, 200 mL) and toluene (200 mL) at −65° to −72° under nitrogen. After a further 30 minutes at −70°, dry dimethylformamide (40 mL) was added during 35 minutes. Stirring continued overnight at −70° to −60°.

Hydrochloric acid (2N, 400 mL) was added, allowing the temperature to rise to about −10°. After 30 minutes, 2N ammonia (ca. 90 mL) was added to pH 7–8. The toluene layer was separated and the aqueous phase was extracted with ether. The combined organic liquids were washed with ice/water, dried (MgSO$_4$) and evaporated in vacuo below 50°. The aldehyde, 2-(6-formyl-2-pyridyl)-2-(4-tolyl)-1,3-dioxolan, (63.9 g) crystallized on keeping at 3°, m.p. 52°–63°.

The aldehyde prepared above (2.5 g) was dissolved in 1,2-dimethoxyethane (10 mL) and added to a solution of the phosphonate carbanion produced from triethyl phosphonoacetate (2 g) and sodium hydride (0.22 g) in the same solvent. The mixture was stirred for two hours, diluted with ether (25 mL) and treated with hydrochloric acid (5 mL, 2M). The organic phase was separated, washed with water, dried, and evaporated. The resulting oil was dissolved in ethanol (20 mL) containing concentrated hydrochloric acid (3 mL) and water (3 mL). After heating on the steam bath for ten minutes, the solution was diluted with ice water, rendered alkaline with sodium bicarbonate solution, and extracted with ether. Evaporation gave (E)-3-[6-(4-toluoyl)-2-pyridyl]acrylic acid which crystallized from cyclohexane in colorless platelets (1 g), m.p. 108°–111°.

Butyllithium (10 mL, 1.64M in hexane) was added under nitrogen to a stirred suspension of triphenyl-2-pyrrolidinoethylphosphonium bromide (7.2 g) in dry toluene (75 mL). After 0.5 hr, (E)-3-[6-(4-toluoyl)-2-pyridyl]acrylic acid, vide supra, (4.8 g) in toluene (50 mL) was added. The suspension, initially orange, became deep purple, then slowly faded to yellow during 2 hours heating at 75°. The cooled solution was diluted with ether (150 mL) and treated with hydrochloric acid (50 mL, 2M). The aqueous phase was separated, washed with ether, and basified with potassium carbonate (ice) and extracted with ether. The mixture of isomeric esters obtained by evaporation was dissolved in ethanol (100 mL) containing sodium hydroxide solution (20 mL, 1M) and partially evaporated on the steam bath under reduced pressure for 5 minutes. The residual aqueous solution was neutralized with sulphuric acid (20 mL, 0.5M) and evaporated to dryness. The solid residue was extracted with hot isopropanol (3×50 mL) and the extracts were concentrated until crystallization commenced. The (E)-3-{6-[3-pyrrolidino-1-(4-tolyl)prop-1E-enyl]-2-pyridyl}acrylic acid (compound 2) after recrystallization from isopropanol, melted at 222° (decomp).

A solution of compound 2, vide supra, (3 g) in alcohol (100 mL) containing Raney nickel (1 g) was stirred under hydrogen at room temperature and pressure until the calculated quantity of hydrogen had been absorbed (ca. 45 minutes). The reduced ester was recovered by filtration and evaporation and purified by column chromatography on silica gel using petroleum ether as eluent. Butyllithium (10 mL, 1.64M in hexane) was added under nitrogen to a stirred suspension of triphenyl-2-pyrrolidinoethylphosphonium bromide (7.2 g) in dry toluene (75 mL) to prepare a Wittig reagent. Treatment of this ester with Wittig reagent by the method of Example 1 followed by saponification gave a mixture of two isomeric acids which were separated by fractional crystallization from ethyl acetate/petroleum ether mixtures. The less soluble E isomer, 3-{6-[3-Pyrrolidino-1-(4-tolyl)prop-1E-enyl]-2-pyridyl}-propionic acid (Compound B), melted at 156°–157°.

EXAMPLE 2:
(E)-3-{6-[3-Dimethylamino-1-(4-tolyl)prop-1E-enyl]-2-pyridyl}acrylic acid Treatment of (E)-3-[6-(4-toluoyl)-2-pyridyl]acrylic acid, vide supra, with the Wittig reagent derived from triphenyldimethylaminoethylphosphonium bromide by the method of example 1 gave a mixture of isomeric acids which were separated by fractional crystallization from ethyl acetate. The less-soluble E-isomer, (E)-3-{6-[3-dimethylamino-1-(4-tolyl)prop-1E-enyl]-2-pyridyl}acrylic acid was purified by crystallization from isopropanol, m.p. 222°–225° (decomp.)

EXAMPLE 3

The following compounds were synthesized by a method similar to that described for compound 2 in example 1, vide supra,:

(a) (E)-3-{6-[3-Pyrrolidino-1-(4-methoxyphenyl)-prop-1E-enyl]-2-pyridyl}acrylic acid, m.p. 231°–232° (Dec), (b) (E)-3-}6-[1-(4-chlorophenyl)-3-pyrrolidinoprop-1E-enyl]-2-pyridyl}acrylic acid, m.p. 218°–220° (Dec), (c) (E)-3-}6-(1-phenyl-3-pyrrolidinoprop-1E-enyl)2-pyridyl}acrylic acid, m.p. 180°–182° (Dec).

EXAMPLE 4:
6-[3-pyrrolidino-1-(4-tolyl)prop-1E-enyl]-pyridine-2-carboxylic acid A solution of (6-bromo-2-pyridyl)-2-(4-tolyl)-1,3-dioxolan (7 g) in dry toluene (80 mL) was added dropwise under nitrogen to a stirred solution of butyl lithium (1.6M in hexane, 20 mL) cooled below −60°. After three hours at this temperature solid carbon dioxide (25 g) was added. The mixture was allowed to warm to 10°, treated with hydrochloric acid (2M, 20 mL) and filtered from a small quantity of solid (3). The toluene layer was separated and concentrated, leaving an oil (7 g). This was heated on the steam bath for ten minutes with 6M hydrochloric acid (10 mL) containing just sufficient alcohol to give a clear solution. Cooling and dilution with water gave a gummy solid which crystallized from water in colourless needles m.p. 151°–3°. (Treatment of the solid 3 with hydrochloric acid afforded a further 0.9 g of the same material). Esterification of this acid with ethanol/sulphuric acid afforded after the usual work up procedure ethyl 6-(4-tolyl)-pyridine-2-carboxylate (Compound 4) (2.8 g) as a colourless oil which slowly crystallized.

Treatment of compound 4, vide supra, with the Wittig reagent derived from triphenyl-2-pyrrolidinoethyl-phosphonium bromide by the method of Example 1 gave, after saponification, a mixture of two geometrical isomers, which were separated by extraction with hot ethyl acetate. The insoluble E-isomer (the title compound), after crystallization from isopropanol, melted at 200°–202°. Cooling of the ethyl acetate solution from Example 3 led to crystallization of the more soluble Z isomer, m.p. 187°–9°.

EXAMPLE 5: Antihistaminic Activity

In vitro antihistaminic activity: The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration-response curve 2X to the right.

TABLE I
Results of Antihistamine Assays

| Compound | $pA_2$ |
|---|---|
| Triprolidine | 10.1 |
| A | 9.2 |
| B | 8.2 |
| C | 8.9 |
| D | 9.0 |
| E | 7.4 |
| F | 8.9 |

EXAMPLE 6: Formulations (A)-Injection

| Ingredient | Amount per ampoule |
|---|---|
| Compound of formula (I) | 1.0 mg |
| Water for Injections, q.s. | 1.0 mL |

The finely ground active compound is dissolved in the water for Injections. The solution is filtered and sterilized by autoclaving.

(B)-Suppository

| Ingredient | Amount per suppository |
|---|---|
| Compound of Formula (1) | 1.0 mg |
| Cocoa Butter, or Wecobee TM Base q.s. | 2.0 g |

Wecobee is a trademark and is a hydrogenated fatty carboxylic acid

The finely ground active compound is mixed with the melted suppository base (either Cocoa Butter or Wecobee TM base), poured into molds and allowed to cool to afford the desired suppositories.

(C)-Syrup

| Ingredient | Amount per 5 mL |
|---|---|
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour q.s. | |
| Coloring q.s. | |
| Water q.s. to | 5.0 mL |

Ethanol, sucrose, sodium benzoate, methylparaben, and flavouring are combined in 70% of the total batch quantity of water. Coloring and the active compound are dissolved in the remaining water, then the two solutions are mixed and clarified by filtration.

(D)-Tablet

| Ingredient | Amount per Tablet |
|---|---|
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

(E)-Capsule

| Ingredient | Amount per Capsule |
|---|---|
| Compound of Formulas (I) | 1.0 mg |
| Lactose | 440.0 mg |
| Magnesium Stearate | 5.0 |

The finely ground active compound is mixed with the powdered excipients lactose, corn starch and stearic acid and packed into two part, gelatin capsules.

(F)-Tablet

| Ingredient | Amount per Tablet |
|---|---|
| Compound of Formula (1) | 1.0 mg |
| Pseudoepbedrine HCl | 60.0 mg |
| Lactose | 62.5 mg |
| Potato Starch | 14.0 mg |
| Magnesium Stearate | 1.0 mg |
| Gelatin | 2.8 mg |

A tablet is prepared from the above formulation by the method previously described in Example 7(D).

(G)-Syrup

| Ingredient | Amount per 5 mL |
|---|---|
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor q.s. | |
| Color q.s. | |

| (G)-Syrup | |
|---|---|
| Ingredient | Amount per 5 mL |
| Glycerol | 500 mg |
| Sucrose | 2000 mg |
| Purified Water q.s. to | 5.0 mL |

A syrup containing other active ingredients in addition to a compound of formula (I) is prepared from the above ingredients by an analogous method to that described for Example 7(C) above.

| (H)-Nasal Spray | |
|---|---|
| Ingredient | Amount per 100.0 mL |
| Compound of Formula (I) | 1 g |
| Sodium Chloride | 0.8 g |
| Preservative | 0.5 g |
| Purified Water q.s. | 100.0 mL |

The preservative is dissolved in warm purified water and after cooling to 25°–30° C. the sodium chloride and the compound of formula (I) are added. The pH is then adjusted to 5.5–6.5 and purified water is added to bring the final volume to 100.0 mL.

| (I)-Opthalmic Solution | |
|---|---|
| Ingredient | Amount per 100.0 mL |
| Compound of Formula (I) | 0.1 g |
| Sodium Chloride | 0.8 g |
| Preservative | 0.5 g |
| Water for Injection q.s. | 100.0 mL |

This formulation is prepared in a similar way to the nasal spray.

| (J)-Topical Cream | |
|---|---|
| Ingredient | Amount per 100.0 mL |
| Compound of Formula (I) | 0.1 g |
| Emulsifying Wax, N.F. | 15.0 g |
| Mineral Oil | 5.0 g |

We claim:

1. A compound of formula (I),

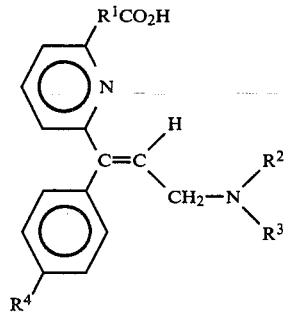

or a straight or branched lower alkyl (1–4 carbon atoms) ester, or a pharmaceutically acceptable salt thereof; wherein $R^1$ is a bond; $R^2$ and $R^3$ are the same or different and can be hydrogen, $C_{1-4}$ alkyl or taken together with the nitrogen together with the nitrogen to which they are attached form a nitrogen containing heterocyclic ring having four to six ring members; $R^4$ is hydrogen, halogen, $C_{1-4}$ alkoxy or $C_{1-4}$ alkyl optionally substituted by one to three halogen atoms.

2. 6-[3-pyrrolidino-1-(4-tolyl)prop-1E-enyl]pyridine-2-carboxylic acid.

3. A compound of claim 1 as the hydrochloride salt.

4. A pharmaceutically acceptable salt of 6-[3-pyrrolidino-1-(4-tolyl)prop-1E-enyl]pyridine-2-carboxylic acid.

* * * * *